US010736985B2

(12) United States Patent
Odermatt et al.

(10) Patent No.: US 10,736,985 B2
(45) Date of Patent: Aug. 11, 2020

(54) MEDICAL DEVICE AND METHOD FOR THE PRODUCTION THEREOF

(71) Applicants: Aesculap AG, Tuttlingen (DE); Carl Freudenberg KG, Weinheim (DE)

(72) Inventors: Erich Odermatt, Schaffhausen (CH); Rainer Bargon, Tuttlingen (DE); Dirk Grafahrend, Mannheim (DE); Daniel Neumüller, Weinheim (DE); Denis Reibel, Herrlisheim (FR)

(73) Assignees: Aesculap AG, Tuttlingen (DE); Carl Freudenberg KG, Weinheim (DE)

( * ) Notice: Subject to any disclaimer, the term of this patent is extended or adjusted under 35 U.S.C. 154(b) by 253 days.

(21) Appl. No.: 15/118,167

(22) PCT Filed: Feb. 12, 2015

(86) PCT No.: PCT/EP2015/052966
§ 371 (c)(1),
(2) Date: Aug. 11, 2016

(87) PCT Pub. No.: WO2015/121350
PCT Pub. Date: Aug. 20, 2015

(65) Prior Publication Data
US 2017/0165394 A1 Jun. 15, 2017

(30) Foreign Application Priority Data
Feb. 12, 2014 (DE) .................. 10 2014 202 578

(51) Int. Cl.
*A61L 15/22* (2006.01)
*A61L 15/64* (2006.01)
*A61L 15/42* (2006.01)
*D01D 5/18* (2006.01)
*D04H 1/70* (2012.01)
*D04H 1/4382* (2012.01)
*D04H 1/30* (2012.01)
*D04H 1/425* (2012.01)
*D01D 5/00* (2006.01)
*A61L 15/32* (2006.01)
*A61L 15/28* (2006.01)
*A61L 15/58* (2006.01)

(52) U.S. Cl.
CPC ............ *A61L 15/225* (2013.01); *A61L 15/28* (2013.01); *A61L 15/325* (2013.01); *A61L 15/42* (2013.01); *A61L 15/58* (2013.01); *A61L 15/64* (2013.01); *D01D 5/00* (2013.01); *D01D 5/18* (2013.01); *D04H 1/4382* (2013.01); *D04H 1/70* (2013.01); *A61L 2400/04* (2013.01); *A61L 2400/12* (2013.01); *D04H 1/30* (2013.01); *D04H 1/425* (2013.01)

(58) Field of Classification Search
CPC ........ A61L 15/225; A61L 15/58; A61L 15/64; A61L 2400/04; A61L 2400/12; A61L 15/42; D01D 5/00; D01D 5/10; D01D 5/18; D01D 5/26; C08L 1/00; C08L 33/02; C08L 39/06; C08L 67/04; C08L 69/00; C08L 89/06; A61F 2/00
See application file for complete search history.

(56) References Cited

U.S. PATENT DOCUMENTS

| | | |
|---|---|---|
| 5,997,895 A | 12/1999 | Narotam et al. |
| 6,197,237 B1 | 3/2001 | Tsai et al. |
| 6,306,782 B1 | 10/2001 | Tsai et al. |
| 6,309,988 B1 | 10/2001 | Tsai et al. |
| 6,544,455 B1 | 4/2003 | Tsai |
| 7,172,765 B2 | 2/2007 | Chu et al. |
| 8,338,402 B2 | 12/2012 | Fry et al. |
| 8,974,815 B2 | 3/2015 | Chu et al. |
| 2002/0090725 A1 | 6/2002 | Simpson et al. |
| 2002/0173213 A1* | 11/2002 | Chu ..................... A61K 9/0024 442/414 |
| 2004/0138609 A1* | 7/2004 | Fukuta .................... A61N 1/30 604/20 |
| 2009/0136651 A1* | 5/2009 | Larsen ................. A61K 38/363 427/2.31 |
| 2009/0148489 A1* | 6/2009 | Cooper ................ A61L 27/446 424/423 |
| 2010/0285291 A1 | 11/2010 | Reibel et al. |
| 2012/0216709 A1 | 8/2012 | Noda et al. |
| 2013/0011676 A1* | 1/2013 | Schmitz ................... D01D 5/18 428/373 |
| 2013/0317611 A1 | 11/2013 | Gelita |
| 2014/0277575 A1* | 9/2014 | Landgrebe ............. D01F 6/625 623/23.72 |

FOREIGN PATENT DOCUMENTS

| | | |
|---|---|---|
| DE | 196 54 884 A1 | 9/1997 |
| DE | 10 2005 048 939 A1 | 1/2007 |

(Continued)

OTHER PUBLICATIONS

Bouten "The chemistry of tissue adhesive materials" Progress in Polymer Science, 39 (2014) 1375-1405, www.elsevier.com (Year: 2014).*

(Continued)

*Primary Examiner* — Jennifer A Steele
(74) *Attorney, Agent, or Firm* — Lewis Kohn & Walker LLP; David M. Kohn

(57) ABSTRACT

A medical device in the form of a nonwoven wound dressing includes rotospun fibers including at least one synthetic and bioabsorbable polymer and at least one hydrophilic and/or tissue-adhesive polymer, and a method of producing the medical device including using rotospinning to produce fibers from a fiber raw material including at least one synthetic and bioabsorbable polymer and at least one hydrophilic and/or tissue-adhesive polymer.

20 Claims, No Drawings

(56) References Cited

FOREIGN PATENT DOCUMENTS

| | | | |
|---|---|---|---|
| DE | 10 2010 012 845 | | 9/2011 |
| DE | 10 2010 012 845 A1 | | 9/2011 |
| EP | 1 025 870 A1 | | 8/2000 |
| EP | 2 042 199 A2 | | 4/2009 |
| EP | 2 147 687 A2 | | 1/2010 |
| WO | WO-2006056740 A3 * | 8/2006 | ........... A61L 27/446 |
| WO | 2007/082295 A2 | | 7/2007 |
| WO | 2008/107126 A1 | | 9/2008 |
| WO | 2009/036958 A2 | | 3/2009 |
| WO | 2009/091549 A1 | | 7/2009 |
| WO | 2009/149181 | | 12/2009 |
| WO | 2010/132636 | | 11/2010 |
| WO | 2012/022422 A1 | | 2/2012 |
| WO | 2012/055494 | | 5/2012 |
| WO | 2012/078472 | | 6/2012 |

OTHER PUBLICATIONS

Taiwanese Office Action dated Feb. 2, 2016, of corresponding Taiwanese Application No. 104104791, along with an English translation.

Amalorpava, M., et al., "Centrifugal spun ultrafine fibrous web as a potential drug delivery vehicle," eXPRESS Polymer Letters, vol. 7, No. 3, 2013, p. 238-248.

Badrossamay, M., et al., "Engineering hybrid polymer-protein super-aligned nanofibers via rotary jet spinning," Biomaterials, vol. 35, 2014, pp. 3188-3197.

Badrossamay, M.R., et al., "Nanofiber Assembly by Rota Jet-Spinning," Nano Letters, Jun. 9, 2010, vol. 10, No. 6, pp. 2257-2261.

Hajiali, H., et al., "Electrospun PGA/gelatin nanofibrous scaffolds and their potential application in vascular tissue engineering," International Journal of Nanomedicine, 2011, vol. 6, pp. 2133-2141.

Written Opinion of the International Searching Authority of corresponding PCT Application No. PCT/EP2015/052966, along with an English translation.

L. John R. Foster et al., "In vitro hydrolytic degradation of centrifugally spun polyhydroxybutyrate—pection composite fibres," Polymer International, vol. 58, Issue 12, Dec. 2009, pp. 1442-1451 (Abstract only).

Mohammad Reza Badrossamay et al., "Nanofiber Assembly by Rotary Jet-Spinning," Nano Letters, vol. 10, No. 6, 2010, pp. 2257-2261. (Abstract only).

English translation of Office Action dated Jul. 3, 2018, of corresponding Japanese Application No. 2-16-551296.

Foster et al., "Centrifugally-spun polyhydroxybutyrate fibres: Effect of process solvent on structure, morphology and cell response." J. Biomater. Sci. Polymer. Edn. (2001) 12(3):317-336.

Badrossamay et al., "Nanofiber Assembly by Rotary Jet-Spinning." (2010) 10(6):2257-2261.

Chinese Office Action dated Dec. 5, 2018, of corresponding Chinese Application No. 201580007953 and English Translation.

Russian Office Action dated Oct. 25, 2018, of corresponding Russian Application No. 2016134236.

* cited by examiner

MEDICAL DEVICE AND METHOD FOR THE PRODUCTION THEREOF

TECHNICAL FIELD

This disclosure relates to a medical device, in particular in the form of a nonwoven wound dressing comprising rotospun fibers, and also to a production method for the medical device.

BACKGROUND

Medical devices in the form of nonwoven fabrics or random-laid webs comprising rotospun gelatin fibers and their use in wound healing or wound covering are known from WO 2008/107126 A1 and WO 2009/036958 A2. An apparatus to produce such rotospun fibers is described in DE 10 2005 048 939 A1.

WO 2012/022422 A1 discloses nonwoven fabrics comprising hydroxypropylcellulose fibers inter alia for wound care or for use as wound dressing.

The use of modified starch for hemostasis is known from WO 2009/091549 A1.

Personal hygiene articles comprising melt-spun composite starch fibers are disclosed in US 2012/0216709 A1.

Multi-ply dural substitutes based on collagen are known from U.S. Pat. No. 5,997,895 A, WO 2007/082295 A2 and EP 2 147 687 A2. EP 1 025 870 A1 further describes a dural substitute based on a copolymer formed from caprolactone and lactide.

DE 196 54 884 A1 discloses a tissue regeneration cover membrane consisting of a synthetic material and a natural material, in particular collagen.

Device categories used for tissue sealing include in principle the following:

The first category relates to sealing devices based on polysaccharides capable of imbibing a large amount of liquid within a short time and hastening blood clotting by concentrating blood platelets. Sealing devices of this type are commercially available, for example, under the designations Tabotamp®, Surgicel®, ChitoFlex® or Perclot®.

The second category of sealing devices relates to collagen devices which in addition to acting similarly to the sealing devices of the first category are thought to stimulate the coagulation cascade by activation of factor XIIa. Corresponding devices are commercially available, for example, under the designations Spongostan® (porcine gelatin), Lyostypt® and DuraGen® (bovine collagen in each case).

The third category relates to liquid sealing devices usually based on synthetic polymers. Examples thereof are hydrogels based on polyethylene glycol derivatives commercially available, for example, under the designations Coseal®, Progel®, Duraseal®, Focalseal® or Bioglue®.

The last category is that of fibrin adhesives. Unlike the sealing devices described above, fibrin adhesives intervene actively in the coagulation cascade and are based on the combined action of the components fibrin, thrombin and aprotinin, which causes blood clotting. Corresponding devices are commercially available, for example, under the designations Evicel®, Tissucol®, Quixil® or Beriplast®.

While tissue-sealing devices of the type in question do in principle deliver satisfactory outcomes, there are some issues.

In sealing devices based on oxidized cellulose, for example, occurrence of infections and tissue irritations and also formation of acidic types of breakdown products can be problematic and disadvantageous for the healing process. A further disadvantage is the generally very burdensome and also environmentally harmful manufacturing process wherein fibrous nonwoven cellulose webs are treated with nitrogen dioxide, which is poisonous and carcinogenic. Even minuscule excursions can lead to some overoxidation and hence to a complete loss of mechanical stability.

Sealing devices based on chitosan have the in-principle disadvantage that chitosan has to be derived from the shells of marine crustaceans, making the manufacturing process costly. Moreover, chitosan has only limited degradability in vivo.

Pulverulent hemostyptics can be disadvantageous in that in the event of particularly strong bleeding they can be washed away from a wound site in the absence of an uninterrupted layer of hemostyptic. What is more, compression of blood vessels is generally not possible from the sole use of powders.

Collagen devices generally require burdensome purifying methods and methods to detect complete deactivation of viruses and prions. There is further some risk of protein-based allergies. In addition, collagen implants can sometimes be the cause of calcifications.

Liquid tissue-sealing devices usually have to be prepared in burdensome syntheses, increasing their cost of manufacture. In addition, these sealing devices generally have to be kept cool and discharged via multi-chamber systems. This adds to the work and time burden of the surgeon. Moreover, many liquid sealing devices lack tensile strength after curing.

Fibrin adhesives are generally costly. The procedures used to derive them on the basis of human blood are usually specially validated, in particular to minimize the risk of infection with HIV, hepatitis C or Creutzfeldt-Jakob. Fibrin adhesives are likewise discharged via multi-chamber systems and therefore have the same disadvantages as described in the preceding paragraph. Moreover, the shelf-life of fibrin adhesives is very limited.

It could therefore be helpful to provide a medical device that circumvents known issues and, in particular, is useful in the sealing of wounds.

We provide a medical device comprising rotospun, i.e., rotation or rotationally spun, fibers. The medical device may be configured in particular as a nonwoven fabric.

The fibers comprise at least two different polymers, namely at least one synthetic and bioabsorbable polymer preferably also hydrophobic, and also at least one further polymer, which is hydrophilic and/or tissue-adhesive.

We found that, surprisingly, synthetic and bioabsorbable polymers are rotospinnable together with hydrophilic and/or tissue-adhesive polymers into multifunctional, in particular bifunctional, medical devices which in principle open up a wide field of medical/medicinal applications but, by virtue of the polymers provided, are particularly suitable for wound sealing.

Namely, the use of hydrophilic polymers allows the development of liquid-imbibing properties, which is advantageous regarding rapid hemostasis in particular. The use of polymers having tissue-adhesive properties in addition or alternatively thereto promotes the formation of devices that are dislocation-resistant, obturating, mechanically stabilizing and also, in particular, act as a germ barrier, this in turn being particularly advantageous regarding a tight and durable wound closure and also avoidance of post-surgical infections.

The use of synthetic and yet bioabsorbable polymers further ensures that our devices are at least partly absorbable in vivo.

The polymers described above additionally make possible, with particular advantage, further uses for the medical device, as will be more particularly described hereinbelow.

Rotospinning additionally has the advantage of providing a multitude of further parameters to precision-engineer the constitution of the fibers and hence the properties of the medical device. For instance, by specifying the speed of rotation, an air and/or material gradient, the discharge hole size in the base of a rotating receptacle (the rotospinneret) and also by applying an electric field, it is possible to actualize a far larger range of fiber diameters than is generally the case with conventional melt-spinning processes. By virtue of the large number of parameters that can be varied, our medical devices are with particular advantage custom-tailorable to specific applications. It is thereby possible, for example, to produce medical devices having a high level of tensile strength (ultimate tensile stress) and, in particular, high elasticity.

A further advantage is that the rotospinning process is relatively simple to police. The physical laws involving the centripetal forces responsible for fiber formation will always ensure reproducible manufacturing conditions. These manufacturing conditions are further readily upscalable, for example, to the use of larger rotospinnerets.

It is finally a particular advantage that the handling properties of the devices are outstanding, in particular by virtue of the properties mentioned in the preceding sections.

The expression "synthetic" means that the polymer so referred to is not a natural product, but the product of what is generally a chemical, in particular industrial or technical, or recombinant (i.e., brought about by recombinant organisms) synthesis.

The expression "bioabsorbable" means that the polymer so referred to is in vivo degraded and absorbed. Degradation preferably proceeds without formation of degradation products that are immunogenic or toxic.

The expression "hydrophilic" means that the polymer so referred to is generally water-loving, i.e., enters a strong interaction with water, in particular via hydrogen bonds, and hence is in line with the usual understanding among persons skilled in the art. More particularly, the expression "hydrophilic" means that the polymer so referred to is water soluble or swellable.

Correspondingly, the expression "hydrophobic" means that the polymer so referred to is water-rejecting, and thus is likewise in harmony with the usual connotation.

The expression "tissue-adhesive" means that the polymer so referred to is capable of forming an adhesive bond with biological, in particular human or animal, tissue layers, for example, a mucin layer of mucosae. The adhesive bond is preferably solely reliant on Van der Waals interactions, electrostatic interactions and/or dipole-dipole interactions. In other words, a tissue-adhesive polymer is preferably capable of forming an adhesive bond with tissues that is not reliant on formation of covalent bonds.

Preferably, the medical device comprises rotospun fibers comprising mutually different fractions of the at least one synthetic and bioabsorbable polymer and/or the at least one hydrophilic and/or tissue-adhesive polymer. The above-described multifunctional properties of the device are brought out to greater advantage as a result.

The medical device may include rotospun fibers having a higher fraction of the at least one synthetic and bioabsorbable polymer than of the at least one hydrophilic and/or tissue-adhesive polymer.

Additionally or alternatively, the medical device includes rotospun fibers having a smaller fraction of the at least one synthetic and bioabsorbable polymer than of the at least one hydrophilic and/or tissue-adhesive polymer.

The medical device may further comprise rotospun fibers comprising at least one synthetic and bioabsorbable polymer, but no hydrophilic and/or tissue-adhesive polymer. The fibers described in this paragraph preferably form an outer surface layer of the device.

The medical device may further comprise rotospun fibers comprising at least one hydrophilic and/or tissue-adhesive polymer, but no synthetic and bioabsorbable polymer. The fibers described in this paragraph preferably likewise form an outer surface layer of the device, in particular an outer surface layer opposite the outer surface layer mentioned in the preceding section.

The medical device preferably includes rotospun fibrous fractions, in particular fibrous layers, differing from each other in relation to the fiber fraction of the at least one synthetic and bioabsorbable polymer and/or the at least one hydrophilic and/or tissue-adhesive polymer. Owing to their fractionation, in particular their layering, such fibers bring out the multifunctional properties of the device even more. Particularly, a medical device having functionally distinguishable fibrous fractions, in particular fibrous layers, is realizable thereby.

The medical device may include at least one rotospun fibrous layer whose fibers comprise a higher fraction of the at least one synthetic and bioabsorbable polymer than of the at least one hydrophilic and/or tissue-adhesive polymer. The at least one fibrous layer preferably comprises an outer surface layer of the device.

Additionally or alternatively, the medical device comprises at least one rotospun fibrous layer whose fibers comprise a smaller fraction of the at least one synthetic and bioabsorbable polymer than of the at least one hydrophilic and/or tissue-adhesive polymer. The at least one fibrous layer preferably comprises an outer surface layer of the device, in particular an outer surface layer that is opposite to the outer surface layer mentioned in the preceding section.

We further provide that the medical device may comprise at least one rotospun fibrous layer whose fibers comprise the at least one synthetic and bioabsorbable polymer, but not the at least one hydrophilic and/or tissue-adhesive polymer. In other words, our medical device may further comprise at least one rotospun fibrous layer whose fibers comprise at least one synthetic and bioabsorbable polymer, but no hydrophilic and/or tissue-adhesive polymer. The at least one fibrous layer preferably likewise comprises an outer surface layer of the device, in particular an outer surface layer that is opposite the outer surface layers mentioned in the preceding sections.

The device may further comprise at least one rotospun fibrous layer whose fibers comprise the at least one hydrophilic and/or tissue-adhesive polymer, but not the at least one synthetic and bioabsorbable polymer. In other words, the device may further comprise at least one rotospun fibrous layer whose fibers comprise at least one hydrophilic and/or tissue-adhesive polymer, but no synthetic and bioabsorbable polymer. The at least one fibrous layer preferably similarly comprises an outer surface layer of the device, in particular an outer surface layer opposite one of the outer surface layers mentioned in the preceding sections, preferably the outer surface layer mentioned in the preceding section.

Particularly preferably, the medical device includes a fiber fraction gradient in relation to the at least one synthetic and bioabsorbable polymer and/or in relation to the at least one hydrophilic and/or tissue-adhesive polymer, more preferably in relation to the at least one synthetic and bioabsorbable polymer and the at least one hydrophilic and/or tissue-adhesive polymer. This makes possible, to particular advantage, a preferably gradual instillation of functional properties of the device, for example, bioabsorbability, tensile strength, liquid imbibition capacity, tissue adhesion capacity and the like.

The fraction of the at least one synthetic and bioabsorbable polymer and/or of the at least one hydrophilic and/or tissue-adhesive polymer in the fibers may change, from a first outer surface of the device in the direction of a second preferably opposite outer surface of the device, preferably gradually, i.e., along a gradient, in a further example. In other words, a fiber fraction gradient preferably extends along the thickness of the device. This enables functional properties of the device, for example, bioabsorbability, tensile strength, liquid imbibition capacity, tissue adhesion capacity and the like, to preferably vary gradually along the thickness of the device.

Preferably, the fraction of the at least one synthetic and bioabsorbable polymer in the fibers increases from the first outer surface of the device in the direction of the second, preferably opposite, outer surface of the device, preferably in a gradual manner, and/or the fraction of the at least one hydrophilic and/or tissue-adhesive polymer in the fibers decreases from the first outer surface of the device in the direction of the second, preferably opposite, outer surface of the device, preferably in a gradual manner.

More preferably, the fraction of the at least one synthetic and bioabsorbable polymer in the fibers increases from the first outer surface of the device in the direction of the second, preferably opposite, outer surface of the device, preferably in a gradual manner, and correspondingly the fraction of the at least one hydrophilic and/or tissue-adhesive polymer in the fibers decreases from the first outer surface of the device in the direction of the second, preferably opposite, outer surface of the device, preferably in a gradual manner.

The fraction of the at least one synthetic and bioabsorbable polymer and/or of the at least one hydrophilic and/or tissue-adhesive polymer in the fibers may change, preferably in a gradual manner, i.e., along a gradient, between a first outer surface layer of the device and a second, preferably opposite, outer surface layer of the device, in a further example.

The fraction of the at least one synthetic and bioabsorbable polymer in the fibers may increase, preferably in a gradual manner, between a first outer surface layer of the device and a second, preferably opposite, outer surface layer of the device in the direction of the second outer surface layer, and/or the fraction of the at least one hydrophilic and/or tissue-adhesive polymer in the fibers decreases, preferably in a gradual manner, between a first outer surface layer of the device and a second, preferably opposite, outer surface layer of the device in the direction of the second outer surface layer. The first outer surface layer is preferably formed by rotospun fibers comprising at least one hydrophilic and/or tissue-adhesive polymer, but no synthetic and bioabsorbable polymer. The second outer surface layer, by contrast, is preferably formed by rotospun fibers comprising at least one synthetic and bioabsorbable polymer, but no hydrophilic and/or tissue-adhesive polymer.

More preferably, the fraction of the at least one synthetic and bioabsorbable polymer in the fibers increases, preferably in a gradual manner, between a first outer surface layer of the device and a second, preferably opposite, outer surface layer of the device in the direction of the second outer surface layer, and correspondingly the fraction of the at least one hydrophilic and/or tissue-adhesive polymer in the fibers decreases, preferably in a gradual manner, between the first outer surface layer of the device and the second, preferably opposite, outer surface layer of the device in the direction of the second outer surface layer. The first outer surface layer is preferably formed by rotospun fibers comprising at least one hydrophilic and/or tissue-adhesive polymer, but no synthetic and bioabsorbable polymer. The second outer surface layer, by contrast, is preferably formed by rotospun fibers comprising at least one synthetic and bioabsorbable polymer, but no hydrophilic and/or tissue-adhesive polymer.

The medical device may comprise a sequence of rotospun fibrous layers wherein the fiber fraction of the at least one synthetic and bioabsorbable polymer and/or of the at least one hydrophilic and/or tissue-adhesive polymer changes, preferably in a gradual manner, along the sequence of layers, i.e., along the sequence of rotospun fibrous layers.

Preferably, the fiber fraction of the at least one synthetic and bioabsorbable polymer increases along the layer sequence, preferably in a gradual manner, and/or the fiber fraction of the at least one hydrophilic and/or tissue-adhesive polymer decreases, preferably in a gradual manner, along the layer sequence.

More preferably, the fiber fraction of the at least one synthetic and bioabsorbable polymer increases along the layer sequence, preferably in a gradual manner, and correspondingly the fiber fraction of the at least one hydrophilic and/or tissue-adhesive polymer decreases, preferably in a gradual manner, along the layer sequence.

Preferably, the medical device comprises a sequence of rotospun fibrous layers between a first outer surface layer and a second, preferably opposite, outer surface layer in each of which the fiber fraction of the at least one synthetic and bioabsorbable polymer increases, preferably in a gradual manner, along the layer sequence in the direction of the second outer surface layer, and/or the fiber fraction of the at least one hydrophilic and/or tissue-adhesive polymer decreases, preferably in a gradual manner, along the layer sequence in the direction of the second outer surface layer. More preferably, the fiber fraction of the at least one synthetic and bioabsorbable polymer increases, preferably in a gradual manner, along the layer sequence in the direction of the second outer surface layer, and correspondingly the fiber fraction of the at least one hydrophilic and/or tissue-adhesive polymer decreases, preferably in a gradual manner, along the layer sequence in the direction of the second outer surface layer. The first outer surface layer is preferably formed by rotospun fibers comprising at least one hydrophilic and/or tissue-adhesive polymer, but no synthetic and bioabsorbable polymer. The second outer surface layer, by contrast, is preferably formed by rotospun fibers comprising at least one synthetic and bioabsorbable polymer, but no hydrophilic and/or tissue-adhesive polymer.

The gradient mentioned in the preceding sections may comprise a continuous or discontinuous, in particular a stepped, gradient.

The layer(s) mentioned above may be 10 µm to 4000 µm, in particular 100 µm to 4000 µm and preferably 500 µm to 2000 µm in thickness.

The fibers may comprise the at least one synthetic and bioabsorbable polymer in a fraction of 1 wt % to 99 wt %, in particular 20 wt % to 99 wt %, preferably 50 wt % to 99 wt %, based on the total weight of an individual fiber.

The fibers may further comprise the at least one hydrophilic and/or tissue-adhesive polymer in a fraction of 1 wt % to 99 wt %, in particular 1 wt % to 80 wt %, preferably 1 wt % to 50 wt %, based on the total weight of an individual fiber.

The medical device may have a fiber fraction gradient of 100 wt % to 30 wt %, in particular 100 wt % to 50 wt % and preferably 100 wt % to 70 wt % per individual fiber in relation to the at least one synthetic and bioabsorbable polymer. The medical device may more particularly have a fiber fraction gradient of 90 wt % to 30 wt % and preferably 80 wt % to 60 wt % per individual fiber in relation to the at least one synthetic and bioabsorbable polymer.

The medical device may have a fiber fraction gradient of 100 wt % to 30 wt %, in particular 100 wt % to 50 wt % and preferably 100 wt % to 70 wt % per individual fiber in relation to the at least one hydrophilic and/or tissue-adhesive polymer. The medical device may more particularly have a fiber fraction gradient of 90 wt % to 30 wt % and preferably 80 wt % to 60 wt % per individual fiber in relation to the at least one hydrophilic and/or tissue-adhesive polymer.

The at least one synthetic and bioabsorbable polymer is preferably selected from the group comprising polylactide, polyglycolide, poly-ε-caprolactone, polytrimethylene carbonate, poly-3-hydroxybutyrate, poly-4-hydroxybutyrate, poly-para-dioxanone, copolymers thereof, derivatives thereof, stereoisomers thereof and mixtures (blends) thereof.

The at least one hydrophilic and/or tissue-adhesive polymer is preferably selected from the group comprising polyacrylic acid, polyvinylpyrrolidones, proteins, polysaccharides, in particular celluloses, mucopolysaccharides, copolymers thereof, derivatives thereof, stereoisomers thereof, salts thereof and mixtures (blends) thereof.

The at least one hydrophilic and/or tissue-adhesive polymer may more particularly be selected from the group comprising cellulose, methylcellulose (approved for use as a food additive under the number E 461), ethylcellulose (approved for use as a food additive under the number E 462), hydroxypropylcellulose (approved for use as a food additive under the number E 463), hydroxypropylmethylcellulose (approved for use as a food additive under the number E 464), methylethylcellulose (approved for use as a food additive under the number E 465), sodium carboxymethylcellulose (approved for use as a food additive under the number E 466), hydroxyethylcellulose, hydroxybutylmethylcellulose, cellulose acetate, cellulose acetobutyrate, cellulose acetomaleate, cellulose acetophthalate, cellulose acetotrimellitate, cellulose fatty acid ester (specifically cellulose dilaurate, cellulose dipalmitate, cellulose distearate, cellulose monopalmitate, cellulose monostearate, cellulose trilaurate, cellulose tripalmitate and/or cellulose tristearate), agar, alginic acid, ammonium alginate, sodium alginate, calcium alginate, the calcium and sodium salts of cellulose carboxymethyl ether, carrageenan, i-carrageenan, κ-carrageenan, λ-carrageenan, starch, acetylated starch, distarch phosphate, specifically acetylated distarch phosphate, pregelatinized starch, carob bean flour, maize (corn) starch, swellable starch, pullulan, dextrin, cellulose 2-hydroxyethyl ether, hydroxyethylmethylcellulose, cellulose 2-hydroxypropyl ether, cellulose 2-hydroxypropyl ether (low degree of substitution), hydroxypropylstarch, ethanol homopolymer, hyaluronic acid, sodium hyaluronate, gelatin, copolymers thereof, derivatives thereof, stereoisomers thereof, salts thereof and mixtures thereof.

The fibers may comprise at least one additive preferably selected from the group comprising plasticizers, fillers, crosslinking agents, dyes, medical actives and mixtures thereof.

In particular, the fibers may comprise the at least one additive at 0 wt % to 10 wt %, in particular 0.05 wt % to 10 wt %, preferably 0.1 wt % to 5 wt % and more preferably 1 wt % to 5 wt %, based on the total weight of an individual fiber.

Suitable plasticizers may be selected from the group comprising alcohols, sugar alcohols, polyalcohols, polyethers, sodium celluloseglycolates, polyvinyl acetate, polyvinylpyrrolidine and mixtures thereof.

Suitable fillers may be selected from the group comprising crosslinked and specifically low molecular weight polyvinyl alcohol, crosslinked polyvinyl acetate, crosslinked polyvinylpyrrolidone (available, for example, under the designation Polyblasdone™), polyvinylureas, dextrans, sodium cellulose, glycolate, crosscaramellose (available, for example, under the designation Ac-Die-Sol™), hydroxyalkylcelluloses, for example, hydroxypropylmethylcellulose, hydroalkylcelluloses, for example, hydroxyethylcellulose, alkylcelluloses, for example, methylcellulose, microcellulose (available, for example, under the designation Avicel™), pectin, gellan, alginates, ion exchangers, for example, on the basis of methacrylate copolymers with divinylbenzene (available, for example, under the designation Tulsion™) and mixtures thereof.

Suitable dyes are in principle approved dyes from the medicinal product, cosmetic or food sector. The dyes may be selected, for example, from the group comprising curcumin, riboflavin, quinoline yellow, tartrazine, Yellow Orange S, carmine, azorubine, Ponceau 4R, erythrosine, Red 2G, Allulared AC, Patent Blue V, indigotin, Brilliant Blue FCF, chlorophyll, caramel, Brown FK, Brilliant Black BN, anthocyanines, xanthophylls, carotenoids, D & C dyes and mixtures thereof.

Suitable medical actives may be selected from the group comprising antimicrobial, specifically antibiotic, actives, disinfecting actives, antiinflammatory actives, hemostyptic actives, odor-controlling actives and mixtures thereof.

Preferably, the medical device includes a fiber fraction gradient in relation to the at least one additive. This is a particularly advantageous way to engineer additional functional properties, for example, flexibility, mechanical stability, coloration and/or medical activity, into the device in a gradual manner.

The fraction of the at least one additive may change, preferably in a gradual manner, i.e., along a gradient, in particular from a first outer surface of the device in the direction of a second, preferably opposite, outer surface of the device. In other words, a fiber fraction gradient in relation to the at least one additive is preferably established along the thickness of the device.

The change in question may take the form of the fraction of the at least one additive in the fibers increasing or decreasing, preferably in a gradual manner, from the first outer surface of the device in the direction of the second, preferably opposite, outer surface of the device.

The medical device may comprise a sequence of rotospun fibrous layers wherein the fiber fraction of the at least one additive changes, specifically increases or decreases, along the layer sequence.

The medical device preferably comprises a sequence of rotospun fibrous layers wherein the fiber fraction of the at least one additive changes, specifically increases or decreases, along the layer sequence in a gradual manner.

The gradient mentioned in the preceding sections may likewise be a continuous or discontinuous, specifically stepped, gradient.

The fibers may be in a mechanically consolidated state to enhance the mechanical stability of the medical device. Mechanical consolidation may be based, for example, on random entanglements or twists of the fibers, which additionally serve to improve the extensibility of the device in the moist state. Alternatively or additionally thereto, the fibers may be mechanically consolidated by hydroentangling, pressing and/or calendering.

The medical device preferably has a tensile strength (ultimate tensile stress) of at least 0.15 N/mm². The device may in particular have a tensile strength of 0.15 N/mm² to 3 N/mm², preferably 0.5 N/mm² to 2 N/mm², more preferably of 1 N/mm².

The fibers may have a diameter of 50 nm to 200 μm, in particular 100 nm to 150 μm, preferably 200 nm to 100 μm (determined by scanning electron microscopy as the mean of 50 individual fibers).

The fibers in opposite outer surface layers of the device may differ in diameter.

The diameter of the fibers may change, preferably in a gradual manner, i.e., along a gradient, in particular from a first outer surface of the device in the direction of a second, preferably opposite, outer surface of the device. In other words, a fiber diameter gradient is preferably established along the thickness of the device.

The change in question may take the form of the fiber diameter increasing or decreasing, preferably in a gradual manner, from the first outer surface of the device in the direction of the second, preferably opposite, outer surface of the device.

The medical device may comprise a sequence of rotospun fibrous layers wherein the diameter of the fibers changes, specifically increases or decreases, along the layer sequence.

The medical device preferably comprises a sequence of rotospun fibrous layers wherein the diameter of the fibers changes, specifically increases or decreases, along the layer sequence in a gradual manner.

The gradient mentioned in the preceding section may likewise comprise a continuous or discontinuous, specifically stepped gradient.

The extensibility of the medical device in the moist state may be 50% to 400%, in particular 100% to 300% and preferably 150% to 200%, based on the original length of the device (in the dry and unextended state).

The medical device may further have a thickness of 0.1 mm to 10 mm, in particular 0.2 mm to 6 mm, preferably from 0.5 mm to 3 mm (determined to ISO 9073-2).

The medical device may further have a basis weight of 10 g/m² to 300 g/m², in particular 20 g/m² to 250 g/m², preferably 40 g/m² to 250 g/m².

The medical device may have an open-cell configuration in the dry state.

In particular, the air permeability (determined to EN ISO 9237) of the medical device in the dry state may be 0.1 l/[min·cm²] to 1 l/[min·cm²], in particular 0.3 l/[min·cm²] to 0.8 l/[min·cm²], preferably 0.3 l/[min·cm²] to 0.7 l/[min·cm²].

The medical device is preferably in vivo absorbable (bioabsorbable) within a period of two years, preferably one year, in particular six months.

The medical device preferably further has a layered configuration or construction.

The medical device may in principle have a textile structure, in particular include or take the form of a textile fabric.

The medical device may, for example, include or take the form of a knitted, woven or braided fabric.

The medical device may further include or take the form of a pseudomonofil or multifil, in particular braided or twisted, thread.

However, it is preferable when the medical device includes or takes the form of a non-textile structure, in particular a non-textile fabric.

The medical device preferably includes or takes the form of a fibrous nonwoven web.

The medical device more preferably includes or takes the form of a nonwoven fabric.

It is further preferable for the medical device to comprise an implant or be intended for use as an implant.

The medical device is more preferably intended for sealing or bonding biological, preferably human or animal, tissue and/or wounds, specifically internal wounds. The device is usable in particular in the approximation of tissue halves separated from each other following surgery, for example.

The medical device is further very suitable for use as a hemostyptic. It is particularly suitable for stopping severe bleeds, in particular bleeds from parenchymatous organs, for example, the lungs, the kidneys, the spleen and/or the liver.

The medical device may further be envisioned as an absorbent for bodily fluids, in particular blood, exudate, pus, liquor and/or lymph.

The medical device may further be provided for application in the sealing of liquid and/or gas leaks in the body of a human or animal patient. Liquid leaks may comprise in particular blood, exudate, pus, liquor and/or lymph leaks. Gas leaks preferably comprise air leaks, in particular in relation to the lungs.

A further preferred application relates to the use of the medical device as an anti-adhesion agent, i.e., as an agent for prevention and/or prophylaxis of postoperative tissue adhesions/adherences.

The medical device is further usable as a germ barrier, in particular for prevention of postsurgical infections.

Further applications relate to the utility of the medical device as a wound bridge to avoid wound dehiscences, to cover a dural defect, as a fascial substitute, as a spongy body for vessel compression and/or tissue overlapping, as a matrix for in vitro and/or in vivo cell colonization and/or as a place holder for endogenous tissue.

We also provide a method of producing a medical device, in particular a medical device.

The method comprises using rotospinning to produce fibers from a fiber raw material comprising at least one first synthetic and bioabsorbable polymer and at least one second hydrophilic and/or tissue-adhesive polymer.

The method may comprise rotospinning to produce fibers from a fiber raw material comprising at least one synthetic and bioabsorbable polymer, but no hydrophilic and/or tissue-adhesive polymer.

The method may comprise rotospinning to produce fibers from a fiber raw material comprising at least one hydrophilic and/or tissue-adhesive polymer, but no synthetic and bioabsorbable polymer.

The fiber raw material is conveniently in a fluid or fluidized form. In principle, the fiber raw material may be provided as a melt, solution, suspension or dispersion.

The fiber raw material may include the at least one synthetic and bioabsorbable polymer at 1 wt % to 99 wt %, in particular 20 wt % to 99 wt % and preferably 50 wt % to 99 wt %, based on the overall weight of the fiber raw material.

The fiber raw material may further include the at least one hydrophilic and/or tissue-adhesive polymer at 1 wt % to 99 wt %, in particular 1 wt % to 80 wt % and preferably 1 wt % to 50 wt %, based on the overall weight of the fiber raw material.

Preferably, the fiber raw material is used to produce fibers by introducing it into a supply container and making the container rotate to use the centripetal forces to discharge the fiber raw material from the container in the form of fibers.

The emerging fibers may be guided in a directed no-contact manner. No-contact and defined guidance of the fibers before they land on a laydown means has the particular advantage of allowing the fibers to be modified. Even just the guidance period or guidance direction can influence fiber length, fiber diameter and also fiber structure. Directed no-contact guidance creates a more homogeneous fiber spectrum than a production process without guidance. A particular advantage is that guidance alone can be used to establish the width of a distribution curve for all the fiber properties. This is a way to appreciably reduce the amount of fibers having an unwanted geometry.

The fibers may emerge from the abovementioned supply container via exit regions preferably configured as passages in the floor region of the container. The exit regions may be 0.1 mm to 2 mm, preferably 0.3 mm to 1 mm and especially 0.3 mm to 0.7 mm in diameter.

The exit regions from the supply container may be, for example, spaced 10 mm apart from each other.

Conveniently, the supply container may be heated to a temperature of 20° C. to 180° C., in particular 20° C. to 100° C., preferably 30° C. to 60° C., more preferably to a temperature of 45° C.

The supply container may be rotated at a speed of 1 rpm to 25 000 rpm, in particular 2000 rpm to 10 000 rpm, preferably 3000 rpm to 7000 rpm.

To establish a fiber diameter gradient, we further provide for a gradual change in the speed of rotation of the supply container.

Conveniently, the fibers are collected on a laydown means.

Fiber production may be assisted by applying an electric field, for example, between a laydown means and a rotatable supply container, in particular as described in the preceding examples.

Advantageously, the fibers may be guided by suction means. This provides for additional drawing or twisting of the fibers and hence an enhancement in individual fiber strengths. It is conceivable for the fibers to be transported by a gas stream. Air is an example of a usable gas. Inert gases, for example, nitrogen are usable as an alternative or in addition.

Particularly preferably, the fraction of the at least one synthetic and bioabsorbable polymer and/or of the at least one hydrophilic and/or tissue-adhesive polymer in the fiber raw material is changed during the rotospinning step in a gradual manner, in particular in a continuous or discontinuous manner, for example, stepwise.

This is realizable, for example, by a rotatable supply container at different feed rates with a first liquid comprising the at least one synthetic and bioabsorbable polymer and with a second liquid comprising the at least one hydrophilic and/or tissue-adhesive polymer. The different feed rates may be the result of gradually increasing the feed rate of the first liquid and gradually reducing the feed rate of the second liquid in a corresponding manner, or vice versa. Alternatively, the feed rate of one of the two liquids may be kept constant while that of the other liquid is gradually increased or reduced.

We further provide that initially only one of the two liquids may be fed into a rotatable supply container, while the feeding of the other liquid into the supply container only takes place after a temporally defined gap. In this example, the feed rate of the one liquid may be increasingly curtailed and specifically cut back to zero, whereas the feed rate of the other liquid is preferably increased in a corresponding manner. This is a particularly advantageous way to produce medical devices having a first outer surface layer and a second, preferably opposite, outer surface layer wherein the fibers of the first outer surface layer comprise the at least one synthetic and bioabsorbable polymer, but not the at least one hydrophilic and/or tissue-adhesive polymer and the fibers of the second outer surface layer comprise the at least one hydrophilic and/or tissue-adhesive polymer, but not the at least one synthetic and bioabsorbable polymer.

The liquids described in the two preceding sections may comprise melts, solutions, dispersions and/or suspensions.

The fiber raw material may further include at least one additive, in particular at a fraction of 0 wt % to 10 wt %, in particular 0.05 wt % to 10 wt %, preferably 0.1 wt % to 5 wt %, more preferably 1 to 5 wt %, based on the overall weight of the fiber raw material.

To establish a fiber gradient in relation to the at least one additive, the fraction of the at least one additive in the fiber raw material may be changed in a gradual manner, in particular in a continuous or discontinuous manner, for example, stepwise during the rotospinning step.

This may be accomplished, for example, by a first liquid comprising the at least one synthetic and bioabsorbable polymer and/or a second liquid comprising the at least one hydrophilic and/or tissue-adhesive polymer being admixed with the at least one additive and fed at different feed rates into a rotatable supply container. The different feed rates may be the result of gradually increasing the feed rate of the first liquid and gradually reducing the feed rate of the second liquid in a corresponding manner, or vice versa. Alternatively, the feed rate of one of the two liquids may be kept constant while that of the other liquid is gradually increased or reduced. The liquids described in this section may in principle likewise comprise melts, solutions, dispersions and/or suspensions.

Particularly advantageously, the rotospun fibers are mechanically compacted or consolidated, preferably in the course of forming a nonwoven fabric. Mechanical compaction or consolidation may be effected by hydroentangling and/or pressing, for example. The step of pressing the fibers may be effected in particular by a Sandt press or a calender.

Regarding further features and advantages of the method, the remarks made in the context of describing the device are referenced in their entirety to avoid repetition.

Further features and advantages will become apparent from the description hereinbelow of preferred examples. The preferred examples are merely offered to assist understanding without limiting the latter thereto.

EXAMPLES

Example 1: Producing a Fibrous Nonwoven Web From Polycaprolactone and Acetylated Distarch Phosphate A first solution was prepared from 20 g of polycaprolactone (PCL) and 80 g of anisole at 80° C. by ultrasonication and occasional stirring. A second solution was prepared from 3 g of acetylated distarch phosphate (6345 Spezialstärke, from Südstärke) and 5 g of dimethyl sulfoxide (DMSO) at 80° C. under agitation.

Both the solutions were cooled down to room temperature (about 25° C.) and fed via two syringe pumps (Harvard syringe pumps 11) to a rotospinneret, where they were homogenized with the assistance of a static mixer. The temperature setting of the rotospinneret for the rotospinning step was 35° C. The speed of rotation of the rotospinneret was 3000 rpm. The floor of the rotospinneret had twelve exit holes having a diameter of 350 µm and a mutual separation of 52 mm. The fibers emerging from the exit holes were collected at room temperature on a laydown support underneath the rotospinneret with the assistance of suction means (750 m³/min). To establish a fiber fraction gradient in relation to the polycaprolactone and the starch, the first solution was fed into the rotospinneret at a constant pumping rate of 10 ml/min, while the pumping rate of the starch solution was gradually raised from 0 to 7.5 ml/min over a period of 10 min.

The fibrous nonwoven web obtained had a thickness of 90 µm (ISO 9073-2), a basis weight of 75 g/m² (ISO 9073-1) as well as a fiber fraction gradient from 100 wt % to 70 wt % per individual fiber in relation to the polycaprolactone. The fibrous nonwoven web exhibited a high level of tensile strength in the dry state and was stable and also readily positionable in the wet state.

Example 2: Producing a Fibrous Nonwoven Web From Polycaprolactone and Acetylated Distarch Phosphate Example 1 was repeated to produce another fibrous nonwoven web except that the second solution was additionally admixed with 0.5 g of polyvinyl alcohol (Mowiol® 20-98) to stabilize the resulting dispersion.

The fibrous nonwoven web obtained had tensile strength in the dry state and was likewise stable and also positionable in the wet state.

Example 3: Producing a Fibrous Nonwoven Web From Polycaprolactone and Cold-Water-Soluble Starch Example 1 was repeated to produce another fibrous nonwoven web except that the 6345 Spezialstärke starch was replaced by Zulkowsky starch (from Sigma-Aldrich).

The fibrous nonwoven web obtained likewise had tensile strength in the dry state and was stable and also positionable in the wet state.

Example 4: Producing a Fibrous Nonwoven Web From Polycaprolactone and Cold-Water-Soluble Starch Example 1 was repeated to produce another fibrous nonwoven web except that Zulkowsky starch (from Sigma-Aldrich) and water was used instead of the 6345 Spezialstärke starch and DMSO.

The fibrous nonwoven web obtained likewise had tensile strength in the dry state and was stable and also positionable in the wet state.

Example 5: Producing a Fibrous Nonwoven Web From Polylactide-co-Glycolide and Cold-Water-Soluble Starch A first solution was prepared from 25 g of Zulkowsky starch (from Sigma-Aldrich) and 27.5 g of DMSO (48%) at 60° C. by ultrasonication. A second solution was prepared from 13 g of polylactide-glycolide copolymer (Resomer RG 504H, from Böhringer Ingelheim), again at 60° C. and by ultrasonication.

Both the solutions were fed at a solution temperature of 60° C. via two syringe pumps (Harvard syringe pumps 11) to a rotospinneret. The temperature setting of the rotospinneret for the rotospinning step was 59° C. The speed of rotation of the rotospinneret was gradually raised from 1500 to 4000 rpm over a period of 15 min. The floor of the rotospinneret had twelve exit holes having a diameter of 350 µm and a mutual separation of 52 mm. The fibers emerging from the exit holes were collected at room temperature on a laydown support underneath the rotospinneret with the assistance of suction means (750 m³/min).

The fibrous nonwoven web obtained had a thickness of 30 µm (ISO 9073-2) and also a basis weight of 20 g/m² (ISO 9073-1). The fibers of the laid-down fibrous nonwoven web had a mean diameter of 1 µm on the bottom outer surface and a mean diameter of 200 nm on the opposite top outer surface. The fibrous nonwoven web had tensile strength and was stable and readily positionable in the wet state.

Example 6: Producing a Fibrous Nonwoven Web From Starch and Polycaprolactone A dispersion was prepared from 6 g of starch (Spezialstärke 6345) and 90 g of anisole under agitation. To the dispersion was added 24 g of polycaprolactone (80 kDa from Sigma-Aldrich) at 80° C. over two hours under agitation. The solution obtained was subsequently allowed to cool down to room temperature.

The solution was syringe pumped at 2 ml/min into a rotospinneret (as described in DE 10 2005 048 939 A1) at a temperature setting of 45° C. The speed of rotation was 3000 rpm. The floor of the rotospinneret had 24 exit holes having a diameter of 800 µm and mutual separation of 26 mm.

The fibrous nonwoven web obtained had a thickness of 30 µm (ISO 9073-2), a mean fiber diameter of 400 nm and also a basis weight of 20 g/m² (ISO 9073-1). The fibrous nonwoven web was weakly hydrophilic and attained its maximum water imbibition capacity within a few minutes. It was further stable and readily positionable in the wet state.

Example 7: Producing a Fibrous Nonwoven Web From Starch and Polycaprolactone A mixture was prepared from 81 g of anisole and 9 g of DMSO. To the mixture was added 6 g of starch under agitation to obtain a dispersion. To the dispersion was then added under agitation at 80° C. 24 g of polycaprolactone (80 kDa from Sigma-Aldrich) over two hours. The solution obtained was allowed to cool down to room temperature.

The rotospinning process used was the same as described in Example 6.

The fibrous nonwoven web obtained had a thickness of 25 µm (ISO 9073-2), a mean fiber diameter of 400 nm and also a basis weight of 20 g/m² (ISO 9073-1). The fibrous nonwoven web was weakly hydrophilic and attained its maximum water imbibition capacity within a few minutes. It was stable and readily positionable in the wet state.

Example 8: Producing a Fibrous Nonwoven Web From Starch/Pullulan/Polycaprolactone A first solution was prepared from 19 g of starch (Zulkowsky potato starch from Sigma-Aldrich), 1 g of pullulan (from Hayashibara Co. Ltd. USP-NF) and 30 g of distilled water by stirring at 60° C. for one hour. A second solution was prepared from 10 g of polycaprolactone and 40 g of anisole by stirring at 80° C. for two hours.

The two solutions were mixed and then syringe pumped at 4 ml/min into a rotospinneret at a temperature setting of 45° C. The speed of rotation was 3000 rpm.

The fibrous nonwoven web obtained had a thickness of 25 µm (ISO 9073-2) and a basis weight of 30 g/m² (ISO 9073-1). The mean fiber diameter was 500 nm. The fibrous nonwoven web was weakly hydrophilic and attained its maximum water imbibition capacity within just a few minutes. The fibrous nonwoven web was also stable in the moist state.

Example 9: Producing a Gradient-Type Fibrous Nonwoven Web Having One Outer Surface Layer of Merely Polycaprolactone and an Opposite Outer Surface Layer of Polycaprolactone and Starch The materials used corresponded to the starting materials used in Example 6. A first solution was prepared as described in Example 6, while a second solution was prepared by dissolving 25 g of polycaprolactone in 100 g of anisole by stirring at 80° C. Both the solutions were then allowed to cool down to room temperature. Two syringe pumps were used to feed the two solutions into a rotospinneret at a temperature setting of 45° C. The speed of rotation was 3000 rpm. To establish a material-type gradient, the feed rate into the rotospinneret was 0 to 2 ml/min for the first solution over three hours and 2 to 0 ml/min for the second solution over three hours.

The fibrous nonwoven web obtained had a thickness of 15 µm and also a basis weight of 20 g/m². The mean fiber diameter was 400 nm. The fibers of the fibrous nonwoven web had a material-type gradient. The fibrous nonwoven web had two functionally distinguishable outer surface layers. While the outer surface layer of polycaprolactone had hydrophobic properties, the opposite outer surface layer had by virtue of its starch fraction hydrophilic properties, which was apparent inter alia from a maximum water imbibition capacity attained in the course of just one minute.

Example 10: Producing a Gradient-Type Fibrous Nonwoven Web From Polycaprolactone/Starch/Pullulan The same materials were used as in Example 8.

A first solution was prepared by dissolving 19 g of starch and 1 g of pullulan in 30 g of distilled water by stirring at 60° C. for one hour. A second solution was prepared by dissolving 20 g of polycaprolactone in 80 g of anisole by stirring at 80° C. for two hours.

The rotospinning process was in this case carried out in two steps. First just 50 g of the second solution were spun as per the process conditions used in Example 1. Then, the first solution and the second solution were syringe pumped into the rotospinneret at a temperature setting of 45° C. The speed of rotation was 3000 rpm. The rate of feed into the rotospinneret was 1:0.2 to 1.8 ml/min for the first solution and 2:0.2 ml/min for the second solution.

The fibrous nonwoven web obtained had a thickness of 30 µm, a mean fiber diameter of 500 µm and also a basis weight of 40 g/m². The fibers of the fibrous nonwoven web had a material-type gradient. The fibrous nonwoven web had two functionally distinguishable outer surface layers. While the outer surface layer of polycaprolactone had hydrophobic properties, the opposite outer surface layer had by virtue of its high starch fraction hydrophilic properties, which was apparent inter alia from a maximum water imbibition capacity attained in the course of just one minute.

Example 11: Producing a Fibrous Nonwoven Web Having One Outer Surface Layer of Polycaprolactone and One Outer Surface Layer Consisting of Polycaprolactone, Carboxymethylcellulose and Polyethylene Glycol The carboxymethylcellulose used was 7H4XF Blanose from Herkules (CAS number: 9004-32-4). The degree of substitution (as per MA 304.1506 A) varied from 0.65 to 0.9, the sodium fraction was between 7.0% and 8.9% and the sulfur ash fraction was between 21.6% and 27.9%.

A first solution was prepared by dissolving 1 g of polyethylene oxide (molecular weight: 1 000 000 g/mol) in water. To the solution was added 7.5 g of 7H4XF Blanose. The mixture was subsequently stirred at room temperature for 24 hours to obtain a solution.

A second solution was prepared by dissolving 25 g of polycaprolactone in 100 g of anisole by stirring at a temperature of 80° C. The solution was subsequently cooled down to room temperature.

Thereafter, the two solutions were fed via two syringe pumps to a rotospinneret at a temperature setting of 45° Celsius. The speed of rotation was 3000 rpm. While the first solution was fed into the rotospinneret at a rate of 1:0 to 2 ml/min for three hours, the second solution was fed into the rotospinneret at a rate of 2:2 to 0 ml/min, again over three hours.

The fibrous nonwoven web obtained had a thickness of 20 µm, a mean fiber diameter of 200 nm and also a basis weight of 20 g/m². The fibers of the fibrous nonwoven web had a material-type gradient. The fibrous nonwoven web had two functionally distinguishable outer surface layers. While the outer surface layer of polycaprolactone had hydrophobic properties, the opposite outer surface layer had by virtue of its carboxymethylcellulose fraction hydrophilic properties. This showed itself inter alia in a maximum water imbibition capacity attained within just one minute and good adherence to various tissues, for example, skin, liver, bone and the like.

Example 12: Producing a Gradient-Type Fibrous Nonwoven Web Having One Outer Surface Layer of Polycaprolactone and One Outer Surface Layer of Polycaprolactone/Povidone A first solution was prepared by introducing 40 g of polyvinylpyrrolidone (Kollidon F90, BASF AG, Germany) into a glass beaker. Then, 160 g of water were added. The mixture was subsequently stirred at room temperature for 24 hours and then heated to 80° C. over one hour. Finally, the solution was ultrasonicated for one hour before being cooled down to 60° C.

A second solution was prepared by dissolving 25 g of polycaprolactone in 100 g of anisole by stirring at 80° C. The solution was subsequently allowed to cool to room temperature.

The two solutions were fed via two syringe pumps to a rotospinneret at a temperature setting of 45° Celsius. The speed of rotation was 3000 rpm. While the first solution was fed into the rotospinneret at a rate of 1:0 to 2 ml/min for three hours, the second solution was fed into the rotospinneret at a rate of 2:2 to 0 ml/min, again over three hours.

The fibrous nonwoven web obtained had a thickness of 50 µm, a mean fiber diameter of 600 nm and also a basis weight of 40 g/m². The fibers of the fibrous nonwoven web had a material-type gradient. The fibrous nonwoven web had two functionally distinguishable outer surface layers. While the outer surface layer of polycaprolactone had hydrophobic properties, the opposite outer surface layer had by virtue of its polyvinylpyrrolidone fraction hydrophilic properties. This showed itself in a maximum water imbibition capacity attained within just one minute and good adherence to various tissues, for example, skin or mucosa.

Example 13: Producing a Fibrous Nonwoven Web Having One Outer Surface Layer of Polycaprolactone and an Opposite Outer Surface Layer of Polycaprolactone/Polyvinyl Alcohol A first solution was prepared by dissolving polyvinyl alcohol (Mowiol 20-98; molecular weight: 125 000 g/mol) in distilled water at 60° C. by stirring for six hours. The solution was subsequently cooled to room temperature.

A second solution was prepared by dissolving 25 g of polycaprolactone in 100 g anisole by stirring at 80° C. The solution was likewise thereafter cooled down to room temperature.

The two solutions were fed via two syringe pumps to a rotospinneret at a temperature setting of 45° C. The speed of rotation was 3000 rpm. While the first solution was fed into the rotospinneret at a rate of 1:0 to 2 ml/min for three hours, the second solution was fed into the rotospinneret at a rate of 2:2 to 0 ml/min, again over three hours.

The fibers of the fibrous nonwoven web obtained had a material-type gradient. The fibrous nonwoven web had two functionally distinguishable outer surface layers. While the outer surface layer of polycaprolactone had hydrophobic properties, the opposite outer surface layer had by virtue of its high polyvinyl alcohol fraction hydrophilic properties. This showed itself inter alia in a maximum water imbibition capacity being attained in just one minute.

Example 14: Producing a Gradient-Type Fibrous Nonwoven Web Having an Outer Surface Layer of Polycaprolactone and an Opposite Outer Surface Layer of Polycaprolactone/Hyaluronic Acid A first solution was prepared by dissolving 12 g of a mixture of 66 wt % Renovhyal hyaluronic acid (molecular weight between 20 kDa and 50 kDa; from Soliance) and 34 wt % of Cristalhyal hyaluronic acid (molecular weight between 1 000 000 g/mol and 1 400 000 g/mol; from Soliance) in 88 g of water at room temperature by stirring for 24 hours.

A second solution was prepared by dissolving 25 g of polycaprolactone in 100 g of anisole by stirring at 80° C. The solution was subsequently cooled to room temperature.

The two solutions were then fed via two syringe pumps to a rotospinneret at a temperature setting of 45° C. The speed of rotation was 3000 rpm. While the first solution was fed into the rotospinneret at a rate of 1:0 to 2 ml/min for three hours, the second solution was fed into the rotospinneret at a rate of 2:2 to 0 ml/min for three hours.

The fibrous nonwoven web obtained had a thickness of 15 µm, a mean fiber diameter of 250 nm and also a basis weight of 10 g/m². The fibers of the fibrous nonwoven web had a material-type gradient. The fibrous nonwoven web had two functionally distinguishable outer surface layers. While the outer surface layer of polycaprolactone had hydrophobic properties, the opposite outer surface layer had by virtue of its high hyaluronic acid fraction hydrophilic properties. This showed itself inter alia in a maximum water imbibition capacity attained within just one minute and good adherence to various tissues, for example, skin, cartilage, bone and the like.

What is claimed is:

1. A medical device in the form of a nonwoven wound dressing comprising rotospun fibers, wherein the fibers comprise at least two different polymers, namely at least one synthetic and bioabsorbable polymer together with at least one further polymer, which is hydrophilic and/or tissue-adhesive, and wherein the device comprises rotospun fibers comprising mutually different fractions of the at least one synthetic and bioabsorbable polymer and the at least one hydrophilic and/or tissue-adhesive polymer wherein the fraction of the at least one synthetic and bioabsorbable polymer and the at least one hydrophilic and/or tissue-adhesive polymer in the fibers change from a first outer surface of the device in the direction of a second opposite outer surface of the device along a gradient.

2. The medical device as claimed in claim 1, wherein the device comprises at least one rotospun fibrous layer whose fibers comprise a higher fraction of the at least one synthetic and bioabsorbable polymer than of the at least one hydrophilic and/or tissue-adhesive polymer.

3. The medical device as claimed in claim 1, wherein the device comprises at least one rotospun fibrous layer whose fibers comprise a smaller fraction of the at least one synthetic and bioabsorbable polymer than of the at least one hydrophilic and/or tissue-adhesive polymer.

4. The medical device as claimed in claim 1, wherein the device comprises at least one rotospun fibrous layer whose fibers comprise the at least one synthetic and bioabsorbable polymer, but not the at least one hydrophilic and/or tissue-adhesive polymer.

5. The medical device as claimed in claim 1, wherein the device comprises at least one rotospun fibrous layer whose fibers comprise the at least one hydrophilic and/or tissue-adhesive polymer, but not the at least one synthetic and bioabsorbable polymer.

6. The medical device as claimed in claim 1, wherein the device comprises a sequence of rotospun fibrous layers wherein a fiber fraction of the at least one synthetic and bioabsorbable polymer and of the at least one hydrophilic and/or tissue-adhesive polymer gradually changes along the sequence of layers.

7. The medical device as claimed in claim 1, wherein the fibers comprise the at least one synthetic and bioabsorbable polymer in a fraction of 1 wt % to 99 wt %, based on the total weight of an individual fiber.

8. The medical device as claimed in claim 1, wherein the fibers comprise the at least one hydrophilic and/or tissue-adhesive polymer in a fraction of 1 wt % to 99 wt %, based on the total weight of an individual fiber.

9. The medical device as claimed in claim 1, wherein the at least one synthetic and bioabsorbable polymer is selected from the group consisting of polylactide, polyglycolide, poly-ε-caprolactone, polytrimethylene carbonate, poly-3-hydroxybutyrate, poly-4-hydroxybutyrate, poly-para-dioxanone, copolymers thereof, derivatives thereof, stereoisomers thereof and mixtures thereof.

10. The medical device as claimed in claim 1, wherein the at least one hydrophilic and/or tissue-adhesive polymer is selected from the group consisting of polyacrylic acid, polyvinylpyrrolidones, proteins, gelatin, polysaccharides, celluloses, mucopolysaccharides, copolymers thereof, derivatives thereof, stereoisomers thereof and mixtures thereof.

11. The medical device as claimed in claim 1, wherein the fibers comprise at least one additive preferably selected from the group consisting of plasticizers, fillers, dyes, medical actives and mixtures thereof.

12. The medical device as claimed in claim 1, wherein the fibers are mechanically consolidated by hydroentangling, pressing and/or calendering.

13. The medical device as claimed in claim 1, wherein the device comprises rotospun fibrous layers differing from each other in relation to a fiber fraction of the at least one synthetic and bioabsorbable polymer and the at least one hydrophilic and/or tissue-adhesive polymer.

14. The medical device as claimed in claim 1, wherein the gradient is a continuous gradient.

15. The medical device as claimed in claim 1, wherein the gradient is a discontinuous gradient.

16. The medical device as claimed in claim 1, wherein the gradient is a stepped gradient.

17. A method of producing the medical device as claimed in claim 1, comprising using rotospinning to produce fibers from a fiber raw material comprising at least two different polymers, namely at least one synthetic and bioabsorbable polymer together with at least one further polymer, which is hydrophilic and/or tissue-adhesive, wherein the fraction of the at least one synthetic and bioabsorbable polymer and of the at least one hydrophilic and/or tissue-adhesive polymer in the fiber raw material is changed during the rotospinning step in a gradual manner, wherein a rotatable supply container is fed at different feed rates with a first liquid comprising the at least one synthetic and bioabsorbable polymer and with a second liquid comprising the at least one hydrophilic and/or tissue-adhesive polymer, wherein the different feed rates are the result of increasing the feed rate of the first liquid along a gradient and reducing the feed rate of the second liquid along a gradient in a corresponding manner, or vice versa, or keeping the feed rate of one of the two liquids constant while that of the other liquid is increased or reduced along a gradient.

18. The method as claimed in claim 17, wherein the gradient is a continuous gradient.

19. The method as claimed in claim 17, wherein the gradient is a discontinuous gradient.

20. The method as claimed in claim 17, wherein the gradient is a stepped gradient.

* * * * *